(12) United States Patent
Brown et al.

(10) Patent No.: US 7,407,953 B2
(45) Date of Patent: Aug. 5, 2008

(54) WOUND HEALING

(75) Inventors: Stanley Beames Brown, Burley-in-Wharfedale (GB); Cassandra Clare O'Grady, Leeds (GB)

(73) Assignee: Photopharmica Limited, Leeds (GB)

( * ) Notice: Subject to any disclaimer, the term of this patent is extended or adjusted under 35 U.S.C. 154(b) by 0 days.

(21) Appl. No.: 11/723,523

(22) Filed: Mar. 20, 2007

(65) Prior Publication Data

US 2007/0161625 A1    Jul. 12, 2007

(51) Int. Cl.
*C07D 279/28* (2006.01)
*A61K 31/5415* (2006.01)
*A61P 17/00* (2006.01)

(52) U.S. Cl. .............. 514/225.2; 514/225.5; 514/225.8; 514/226.2; 544/37

(58) Field of Classification Search ............ 544/37; 514/225.2, 225.5, 225.8, 226.2
See application file for complete search history.

(56) References Cited

U.S. PATENT DOCUMENTS

| | | | |
|---|---|---|---|
| 6,107,466 A | 8/2000 | Hasan et al. | |
| 2002/0187935 A1 | 12/2002 | Redmond et al. | |

FOREIGN PATENT DOCUMENTS

| | | | |
|---|---|---|---|
| CN | 1244391 | | 2/2000 |
| DE | 488945 | * | 1/1930 |
| EP | 0 575 976 A1 | | 12/1993 |
| WO | WO 93/21992 | | 11/1993 |
| WO | WO 00/30630 | | 6/2000 |
| WO | WO 00/40277 | | 7/2000 |
| WO | WO 01/58495 A2 | | 8/2001 |
| WO | WO 02/096896 A1 | * | 12/2002 |

OTHER PUBLICATIONS

K. W. Loach, J. Chromatogr., 60 (1971), 119-126.*
S. J. Valenty, Journal of Colloid and Interface Science, vol. 68, No. 3, Mar. 1, 1979.*
Heckenkamp et al. Journal of Vascular Surgery, vol. 31, No. 6, pp. 1168-1176 (2000).*
Demirov et al. (1989) Our experience in treating sub crustam skin burns, Chirugia, 42(1):38-40.
Heckenkamp et al. ((2000) Local photodynamic action of methylene blue favorably modules the postinterventional vascular wound healing response, J. Vasc. Surg. 31(6):1168-1176.
Pintér et al. (1969) Dünnschichtchromatographischer nachweis einiger farbstoffe für kosmetika nebeneinander, Parfümerie and Kosmetik, 50(4):129-134.

* cited by examiner

*Primary Examiner*—Kahsay T Habte
(74) *Attorney, Agent, or Firm*—Morgan, Lewis & Bockius LLP

(57) ABSTRACT

A phenothiazinium compound, compositions and medicaments for use in promoting wound healing and a method for promoting wound healing or cosmetic use by applying or administering a phenothiazinium compound of Formula (1)

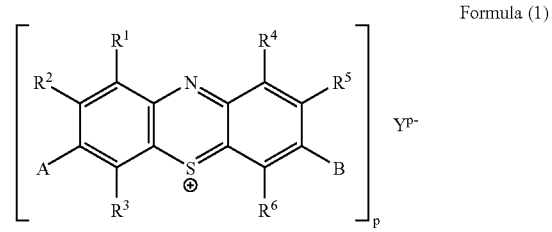

to a wound site or the skin, and optionally exposing the wound site or skin to light.

3 Claims, 4 Drawing Sheets

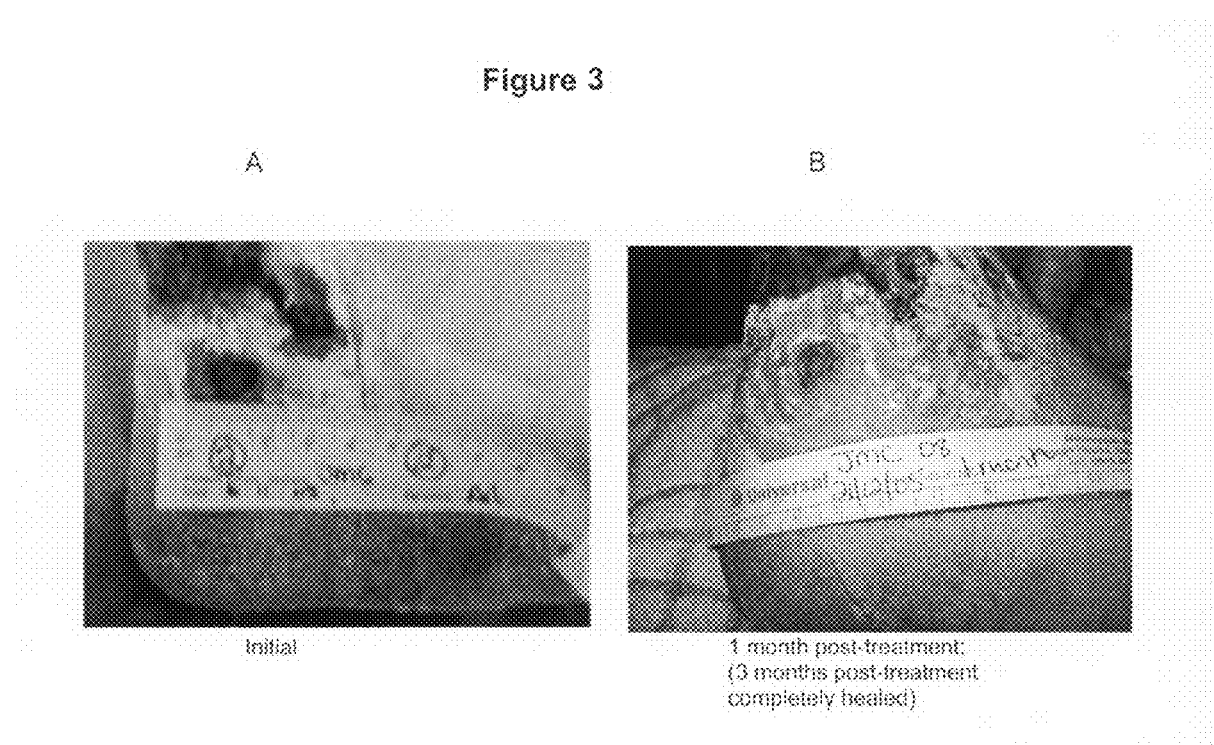

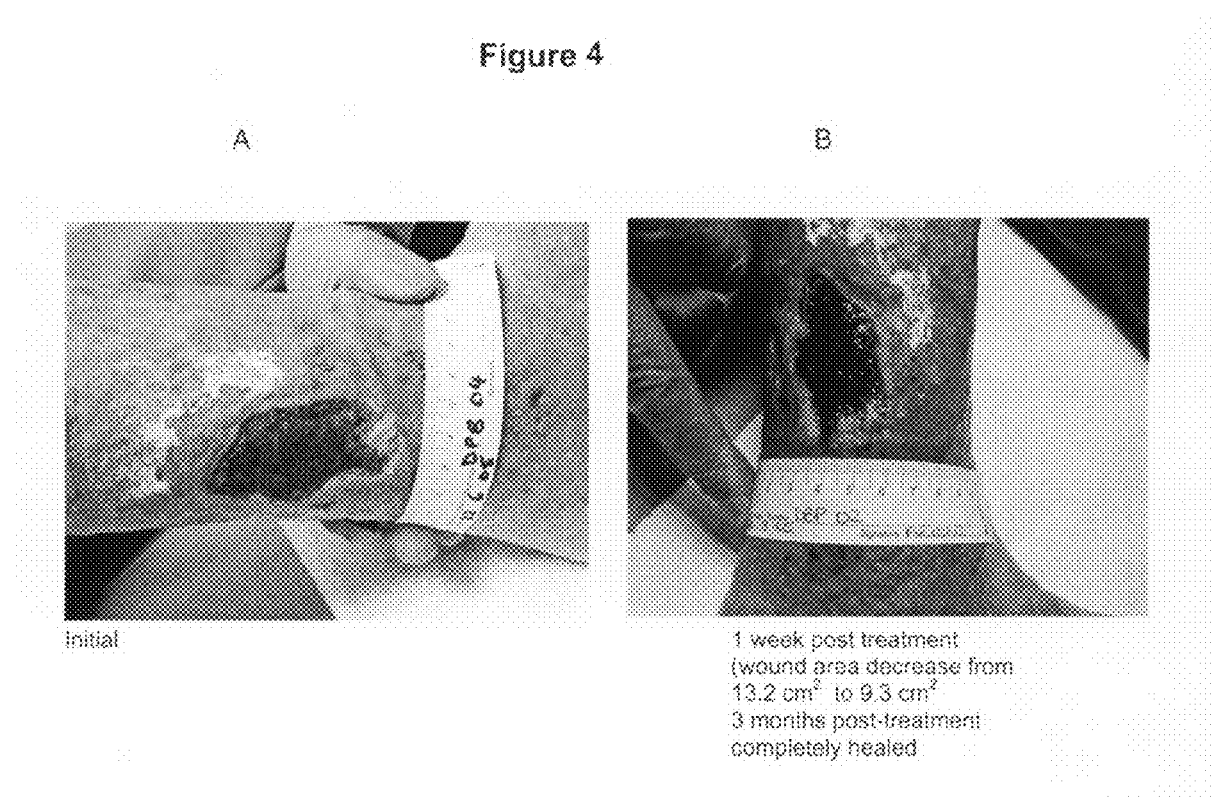

WOUND HEALING

FIELD OF THE INVENTION

This invention relates to wound healing, the use of certain heterocyclic compounds and compositions and medicaments containing them in a wound healing process and for cosmetic uses.

BACKGROUND INFORMATION

The rate of chronic and acute wound healing can be delayed or impaired by a number of factors (exogenous and endogenous) and a variety of medical conditions. Examples include infection, ulceration particularly through diabetes, circulation problems associated with vascular disease, malnutrition, stress, cancer radiotherapy and/or chemotherapy, compromise of the immune system or simply due to the normal aging process. At present there is a clear need for therapeutic and cosmetic approaches that promote wound healing processes.

The literature describes the PDT use of various photosensitisers in attempts to improve wound healing. For example, Photofrin (a porphyrin, Photofrin is a trade mark of Johnson & Johnson) showed delayed wound healing in rat skin flap reconstruction (Kubler et al Lasers in surgery and Medicine (1996), 18(4), 397-405. Parekh et al concluded in Lasers in surgery and Medicine (1999), 24(5), 375-381 that a benzoporphyrin and a phthalocyanine didn't alter wound healing. Lambrects et al concluded in Photochemical & Photobiological Sciences (2005), 4(7), 503-509 that a porphyrin delayed wound healing. Hamblin concluded in Journal of infectious diseases (2003), 187(11), 1717-25 that for a photosensitiser (Poly-lysine-chlorin e6) topical PDT did not accelerate wound healing, compared with that in untreated wounds. Belmont et al in the Laryngoscope (1999), 109(6), 886-90 using Photofrin concluded that PDT has been shown to delay wound healing. Heckenkamp et al in Journal of vascular surgery, (2000), 31(6), 1168-77 concludes that local photodynamic action of methylene blue exerts a retarding effect on intimal hyperplasia (one of the natural wound healing processes).

Compounds, methods and compositions/medicaments have now been identified which address these problems and provide a basis for promoting the wound healing process.

BRIEF DESCRIPTION OF THE DRAWINGS

The following figures represent exemplary embodiments of the invention and are not intended to be limiting.

FIGS. 3A and 3B depict results involving chronic leg ulcer. The wound had shown no response to conventional treatments for 14 months prior to treatment with 3,7-bis(N,N-dibutylamino)phenothiazin-5-ium bromide and PDT.

FIGS. 4A and 4B depict results involving chronic leg ulcer. The wound had shown no response to conventional treatments for 3 months prior to treatment with 3,7-bis(N,N-dibutylamino)phenothiazin-5-ium bromide and PDT.

SUMMARY OF THE INVENTION

Figure 1:
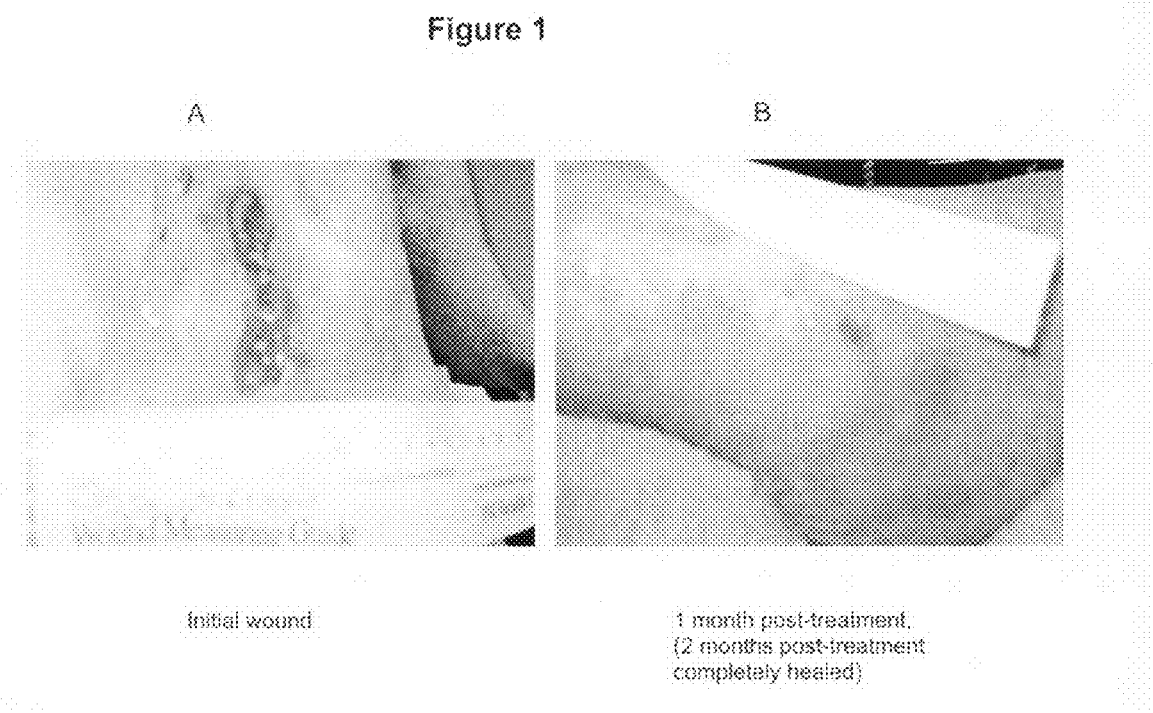
FIGS. 1A and 1B depict the results involving chronic leg ulcer. The wound had shown no response to conventional treatments for 18 months prior to treatment with 3,7-bis(N,N-dibutylamino)phenothiazin-5-ium bromide and PDT.
Figure 2:
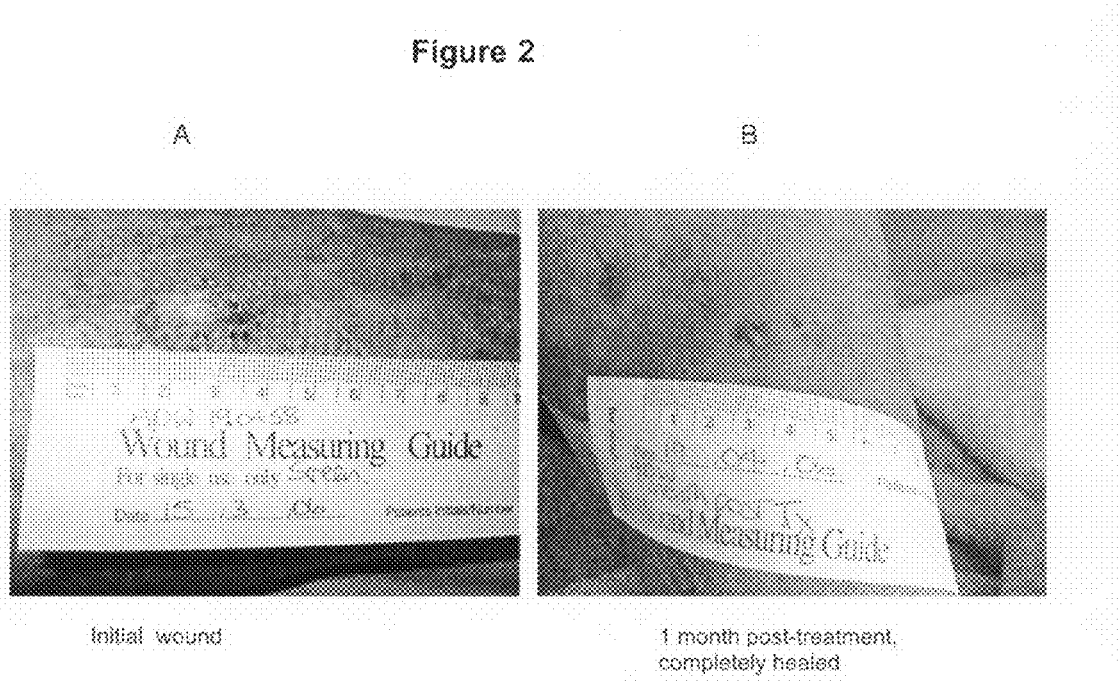
FIGS. 2A and 2B depict results involving chronic leg ulcer. The wound had shown no response to conventional treatments for 7 months prior to treatment with 3,7-bis(N,N-dibutylamino)phenothiazin-5-ium bromide and PDT

According to the present invention there is provided a phenothiazinium compound of Formula (1) for use in promoting wound healing, in which the phenothiazinium compound is of Formula (1):

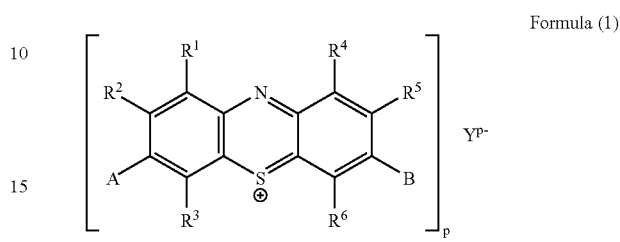

Formula (1)

wherein:
$R^1$-$R^6$ each independently is selected from H, optionally substituted $C_{1-8}$-alkyl, F, Cl, Br and I;
A and B each independently is selected from:

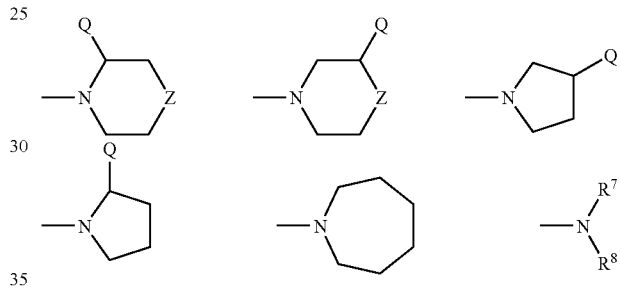

in which:
Q is selected from H and optionally substituted $C_{1-8}$-alkyl;
Z is selected from $C(R^a)_2$, O, S, $SO_2$, $NR^a$ in which each $R^a$ independently is selected from H and optionally substituted $C_{1-8}$-alkyl;
$R^7$ and $R^8$ each independently is selected from H and optionally substituted $C_{1-8}$-alkyl;
Y is a counteranion; and
p is 1, 2 or 3.
Where any one of $R^1$-$R^8$, $R^a$ or Q is optionally substituted alkyl the optional substituents are preferably selected from aryl, particularly Ph; F; Cl; Br; I; OH;
$OC_{1-4}$-alkyl, particularly $OCH_3$, $OC_2H_5$, $OC_3H_7$; CN; $OCOC_{1-4}$-alkyl, particularly $OCOCH_3$; optionally substituted $C_{3-6}$-cycloalkyl, particularly cyclohexyl, methyl-substituted cyclohexyl, cyclopentyl, and methyl-substituted cyclopentyl; COOH; $COOC_{1-4}$-alkyl; $SO_3H$;
The alkyl groups represented by $R^1$-$R^8$, $R^a$ or Q may be straight or branched chain and may optionally include C—C double or triple bonds.
$R^1$-$R^6$ each independently is preferably selected from H, $CH_3$, F, Cl, Br and I.
Where A and B are both $NR^7R^8$, $R^7$ and $R^8$ each independently preferably is selected from H and $C_{1-6}$-alkyl optionally substituted by Ph, F, Cl, Br, I, OH, $OCH_3$, $OC_2H_5$, $OC_3H_7$, CN, $OCOCH_3$, cyclohexyl, methyl-substituted cyclohexyl, cyclopentyl, and methyl-substituted cyclopentyl.
Q is preferably H or $CH_3$.
Z is preferably selected from $CH_2$, O, S, $SO_2$, NH, $NCH_3$, $NC_2H_5$, $NCH_2CH_2OH$ and $NCOCH_3$.

$R^a$ is preferably selected from H, $CH_3$, $C_2H_5$, $CH_2CH_2OH$ and $COCH_3$.

Y may be an organic or inorganic counteranion is preferably selected from $F^-$, $Br^-$, $Cl^-$, $I^-$, $NO_3^-$, $SCN^-$, $ClO_3^-$, $ClO_4^-$, $IO_3^-$, $BF_4^-$, $HSO_4^-$, $H_2PO_4^-$, $CH_3SO_4^-$, $N_3^-$, $So_4^{2-}$, $HPO_4^{2-}$, $PO_4^{3-}$, acetate, lactate, citrate, tartrate, glycolate, glycerate, glutamate, β-hydroxyglutamate, glucouronate, gluconate, malate and aspartate.

In compounds of Formula (1) where one or both of A and B is

one or both of $R^7$ and $R^8$ together with the nitrogen atom to which they are attached may form an optionally substituted 5-, 6- or 7-membered ring.

In compounds of Formula (1) the groups $R^1$ and $R^2$ and/or $R^4$ and $R^5$ together with the carbon atoms to which they are attached may form an optionally substituted 5-, 6- or 7-membered ring.

The rings formed from one or both of $R^7$ and $R^8$ together with the nitrogen atom to which they are attached and from the groups $R^1$ and $R^2$ and/or $R^4$ and $R^5$ together with the carbon atoms to which they are attached may be saturated or unsaturated.

The optional substituents for the optionally substituted 5-, 6- or 7-membered rings formed from $R^7$ and $R^8$ together with the nitrogen atom to which they are attached, and formed from the groups $R^1$ and $R^2$ and/or $R^4$ and $R^5$ together with the carbon atoms to which they are attached may be selected from any of those substituents described above for $R^1$.

Preferably methylene blue and ring substituted derivatives thereof and toluidine blue are excluded from the compounds of Formula (1).

According to a feature of the present invention there is provided a compound of Formula (1) for use as a wound healing agent.

According to a feature of the present invention there is provided a wound healing agent comprising a compound of Formula (1) and a pharmaceutically acceptable diluent or excipient.

The present invention also provides a composition, preferably a pharmaceutical composition, for use in promoting wound healing that comprises a phenothiazinium compound of Formula (1) together with a diluent or excipient.

According to a further feature of the present invention there is provided a use of a compound according to Formula (1) in the manufacture of a medicament for promoting wound healing.

DETAILED DESCRIPTION

The medicament may be in a form for topical or systemic use and is preferably in a form for topical use.

The medicaments are preferably administered topically more preferably administered as a cream, suspension, emulsion, gel, ointment, salve, stick, soap, paste, or via an antimicrobial dressing such as a bandage impregnated with a compound of Formula (1) or a composition or medicament comprising a compound of Formula (1).

The wound healing agents, compositions and medicaments provided by the present invention may comprise mixtures of two or more different compounds of Formula (1); they may also further comprise one or more different therapeutic or active agents.

According to a further feature of the present invention there is provided a method for promoting wound healing in both chronic and acute wounds by applying or administering a phenothiazinium compound of Formula (1) to a wound site, and optionally exposing the wound site to light.

More specifically the method for promoting wound healing includes the following steps:
a) preparing a composition or medicament comprising a compound of Formula (1);
b) applying or administering an effective amount of the composition or medicament to a wound area to be treated: and
c) optionally exposing the wound area to light.

The compounds, compositions, wound healing agents and medicaments of the present invention may be used to treat any condition where the integrity of tissue is damaged, and thus covers chronic and acute wounds, wounds in connective tissue and wounds in muscle, bone and nerve tissue.

The wounds may include, but are not limited to the following: surgical wounds; bites; burns; acid and alkali burns; cold burn (frostbite), sun burn, minor cuts, major cuts, abrasions, lacerations, wounds caused by gunshot or knife injury; wounds caused by congenital disorders; wounds following dental surgery; periodontal disease; wounds following trauma; tumour associated wounds, which can be classified as malignant cutaneous ulcers related to the primary tumour or metastases; ulcers, leg ulcers; foot ulcers; pressure sores and corneal wounds.

Wounds can be classified by having either an acute or chronic etiology. Acute wounds are caused by external damage to intact skin and include surgical wounds, bites, burns, cuts and abrasions, as well as more traumatic wounds such as lacerations and those caused by crush or gun shot injuries.

Chronic wounds are most frequently caused by endogenous mechanisms associated with a predisposing condition that ultimately compromises the integrity of dermal or epithelial tissue. Pathophysiological abnormalities that may dispose to the formation of chronic wounds such as leg ulcers, foot ulcers, and pressure sores include compromised tissue perfusion as a consequence of impaired arterial supply (peripheral vascular disease) or impaired venous drainage (venous hypertension) and diseases such as diabetes mellitus. Advancing age, obesity, smoking, poor nutrition and immunosuppression associated with disease (e.g., AIDS) or drugs (e.g. chemotherapy or radiation therapy) may also exacerbate chronic ulceration. Pressure or decubitis ulcers have a different etiology from other chronic wounds in that they are caused by sustained external skin pressure, most commonly in the buttocks, sacrum, and heels. All chronic wounds heal slowly and in an unpredictable manner (Bowler et al., Clinical Microbiology Reviews, 14 (2) 244). For example, in a study of diabetic foot ulcers, with 20 weeks of good wound care only 31% of the ulcers healed (Margolis, et al. Diabetes Care, 22 (5), 692).

The present compounds, compositions, wound healing agents and medicaments, and method for promoting wound healing may be used any time from wound identification to treat chronic and acute wounds. For wounds that are associated with surgical interventions, such times include pre-, during or post surgery, prior to surgical repair, and post surgical repair, to aid wound healing, preferably at a time from 0 to 7 days after, more preferably from 2 to 6 days after applying or administering the compound of Formula (1). After application or administration of the compound, composition, wound healing agent or medicament to the area to be treated, the area to be treated is optionally exposed to light, and where exposed to light, the time between application or administration of the compound and exposure to light is as defined below. They may also be used any time pre-, during or post in surgical procedures for example: tissue welding, skin grafting and tissue grafting including grafting used in transplant surgery. They may be used to heal inflammatory disorders of the skin that result in itching, crusting, scaling or blisters, such as eczema, psoriasis and acne. The method invention may also be used to treat forms of eczema for example those that result from a weakened immune response (allergy) such as atopic dermatitis.

Application or administration of the compounds, compositions, wound healing agents and medicaments may need to be repeated and typically from 1 to 20 treatments may be applied, more preferably from 1 to 5 treatments to promote wound healing.

The compounds, compositions, wound healing agents, medicaments and methods described herein are preferably used for treating epithelial wounds, more preferably for treating skin wounds.

According to a further feature of the present invention there is provided a cosmetic agent for example for uses in skin rejuvenation and thickening, reducing scar formation and birth mark removal.

According to a further feature of the present invention there is provided a method that may be used for cosmetic purposes, including, but not limited to, skin rejuvenation and thickening, reducing scar formation and birth mark removal. The cosmetic method includes the following steps:

a) preparing a composition comprising a compound of Formula (1);
b) applying or administering an effective amount of the composition to an area to be treated: and
c) optionally exposing the wound area to light.

Where the wound is an internal wound, such as a stomach ulcer, the compound, composition, wound healing agent or medicament may be applied via an endoscope and where it is desirable to expose the wound site to light this may be achieved by use of an endoscopic light source.

The compound of Formula (1) may be applied directly to the wound site or in a pharmaceutically acceptable composition, wound healing agent or medicament. The compound, composition, wound healing agent or medicament may be administered locally or topically and delivered via a variety of means, for example via a spray, local injection, local infusion, cream, lotion, suspension, emulsion, gel, ointment, salve, stick, soap, liquid aerosol, powder aerosol, drops, paste, endoscopically or antimicrobial dressings such as bandages. Preferably administration is topical, more preferably as a cream, suspension, emulsion, gel, ointment, salve, stick, soap, paste, or via an antimicrobial dressing, and especially as a cream, suspension, emulsion, gel or ointment.

The compounds of Formula (1) may be formulated into a variety of pharmaceutical compositions, wound healing agents or medicaments which contain the compounds and pharmaceutically acceptable carriers, excipients, adjuvants (each selected for certain characteristics that permit optimal formulation); these may include liposomes, nanoparticles, colloidal suspensions, micelles, microemulsions, vesicles and nanospheres.

The compositions, wound healing agents or medicaments may also comprise further components such as conventional delivery vehicles and excipients including organic liquids such as alcohols (for example ethanol, propanol and isopropanol), dimethyl sulphoxide, glycols such as propylene glycol and polyethylene glycol, liquid, semi-solid and solid paraffins, water, saline, solubilisers such as castor oil derivatives for example ethoxylated castor oils like Cremophor EL (trade mark BASF AG) or Tween (trade mark, ICI Americas Inc.) types, Unguentum (trade mark, Merck KGaA), Solutol (trade mark, BASF AG), isotonising agents such as urea, glycerol, aminoethanol, propylene glycol, pH regulators, dyes, gelling agents, thickeners, buffers, hydrocarbon waxes and combinations thereof. The compositions of the invention may also optionally include other carriers, stabilizers, preservatives or adjuvants. For typical examples of these classes of compounds, see *Remington: The Science and Practice of Pharmacy*, Lippincott, Williams & Wilkins (2005), which is incorporated by reference in its entirety.

The composition, wound healing agents or medicaments may further comprise a mild reducing agent for example a sugar such as glucose or dextrose; ascorbic acid; sodium metabisulphite and nicotinamide adenine dinucleotide (NADH).

Typically the compositions, wound healing agents or medicaments are prepared by mixing a compound of Formula (1) with one or more pharmaceutically acceptable carriers at an appropriate temperature, typically from 15° to 40° C. at an appropriate pH, typically from pH 3 to 9 and preferably at a physiologically acceptable pH such as from pH 6.5 to 7.5.

The concentration of the compounds of Formula (1) in the compositions, wound healing agents or medicaments depends on the compound's photosensitising ability and is typically in the range from 0.001 to 20%.

Dry compositions, wound healing agents or medicaments which may be reconstituted before use, are also provided in the present invention. These may be prepared by dry mixing solid components or preparing a liquid composition which is evaporated to dryness generally under mild conditions under vacuum or in low temperature ovens, freeze drying is a suitable drying technique.

The compounds of Formula (1) may also be administered systemically by any convenient means, for example intravenously, orally, sub-cutaneously, intramuscularly, directly into affected tissues and organs or intraperitoneally.

Application or administration by any of the means described above may need to be repeated and typically from 1 to 20 treatments may be applied, more preferably from 1 to 5 treatments to promote wound healing.

The dose rate of the compounds of Formula (1) for topical, direct or systemic administration is preferably in the range from 0.1 to 2000 μmol, preferably in the range 10 to 1000 μmol, more preferably from 50 to 500 μmol. For systemic administration such as by injection typical injections volumes are in the range 0.1 to 100 ml, preferably from 5 to 50 ml.

Where wound healing is promoted on exposure to light the light is preferably at wavelengths of 600-800 nm, more preferably at wavelengths from 630 nm to 700 nm The light source may be any appropriate light source such as light emitting diode (LED), a laser or laser diode, a broad spectrum halogen lamp, or filtered lamp.

The light dose administered during PDT can vary but preferably is from 1 to 200 J/cm$^2$, more preferably from 5 to 100 J/cm$^2$, especially from 5 to 75 and ideally from 5 to 25 J/cm$^2$.

Wound healing promotion may be achieved by applying or administering the drug alone or by applying or administering the drug and exposing to light.

Generally, where light exposure is given this may be at the time of drug administration or up to 12 hours after drug administration and the time may be tailored according to the wound being treated, the method of drug delivery and the specific compound of Formula (I) used. Light exposure is preferably given at any time from the time of drug administration up to 3 hours, more preferably from the time of drug administration up to 1 hour. Where the phenothiazinium compound is administered topically the wound is preferably left occluded in the dark for up to 1 hour, more preferably from 1 to 20 minutes, and especially from 8 to 12 minutes before exposure to light.

Wound healing promotion may also be achieved by applying or administering the drug and exposing to light over many hours, for example where the drug is applied to a wound and a light source is included in a wound covering or dressing applied to the wound. Where light is applied over many hours this typically is a lower intensity light. The period where light is applied may be from 1 second to 100 hours.

Increasing the intensity (fluence rate) of the light dose generally reduces light exposure times.

It is preferred that exposure to light is localised to the area/region to be treated, and where wounds are being treated more preferably localised to the wound itself.

After applying or administering the drug the wound may also be exposed intermittently to light, for example light exposures of 1 second up to 72 hours may be used with intermittent periods of 1 second up to 72 hours where there is no light exposure The compounds of Formula (1) and compositions, wound healing agents and medicaments comprising compounds of Formula (1) may be used in the dark or on exposure to light to promote wound healing. In the dark it is the compound of Formula (1) alone that promotes wound healing.

In preferred embodiments of the present inventions wound healing promotion is achieved by applying or administering the drug and exposing to light.

The phenothiazinium salts of Formula (1) may be synthesised as follows:

1) Symmetrical phenothiazinium compounds where A=B
   a) Phenothiazine is firstly brominated with bromine in glacial acetic acid to give 3,7-dibromophenothiazin-5-ium bromide, the suspension formed is collected by filtration.
   b) the 3,7-dibromophenothiazin-5-ium bromide is added to an amine represented by $R^7R^8NH$ (in which $R^7$ and $R^8$ are as defined above) or an N-heterocycle in chloroform. The solid formed is collected by filtration and purified by any suitable means such as by flash column chromatography over silica gel 60, using chloroform, chloroform/methanol (98/2) and then chloroform/methanol (90/10). The product may be further purified by precipitation from chloroform with petroleum ether (b.p. 60-80° C.).

2) Unsymmetrical phenothiazinium compounds where A≠B
   a) Phenothiazine in chloroform is cooled to below 5° C. and a solution of iodine in chloroform added. The solid formed is collected by filtration, washed with chloroform until free of iodine and then kept at room temperature under vacuum overnight to give phenothiazin-5-ium tetraiodide hydrate.
   b) the phenothiazin-5-ium tetraiodide hydrate in methanol is added to a solution of an amine $R^7R^8NH$ (in which $R^7$ and $R^8$ are as defined above). The reaction mixture is stirred overnight, reduced by evaporation and left to cool. The solid that formed is collected by filtration, washed with diethyl ether and dried.
   c) triethylamine in dichloromethane followed by a solution of a different second amine $R^7R^8NH$ (in which $R^7$ and $R^8$ are as defined above) in dichloromethane is added to a solution of the solid from b) above in dichloromethane.

The reaction mixture is stirred overnight, the organic layer washed with dilute hydrochloric acid and water, separated and dried ($MgSO_4$). The majority of the solvent is evaporated and diethyl ether added to precipitate the product which is collected by filtration, washed with diethyl ether and dried. Further purification of the product, if necessary, may be by flash column chromatography as described in 1b) above.

EXAMPLES

Example 1

A Study to Investigate the Effect of 3,7-Bis(N,N-Dibutylamino)Phenothiazin-5-Ium Bromide PDT on Wound Healing in Spontaneous Diabetic Mutation (Strain c57BLKs/Bom db/db Obtainable from Taconic, Denmark) Mice Background When wounds are created on non diabetic (db/+) mice they heal quickly.

When wounds are created on (db/db) diabetic mice the wounds heal more slowly compared to the non diabetic mice. This delayed healing may be caused by a lack of vasculature to feed the wound. The delayed healing model is representative of a chronic wound, and wound healing effects of drugs can be more closely monitored and more easily measured.

Materials and Methods 18 animals were included in this study. 6 control non diabetic mice (db/+), 6 control diabetic (db/db) mice and 6 (db/db) PDT treated diabetic mice.

The 3,7-bis(N,N-dibutylamino)phenothiazin-5-ium bromide was formulated in ethanol and Unguentum M as described in Example 2 below at a concentration of 0.266 mg/mL.

Procedure

On day 0, the animals were anaesthetised and a single standardised full thickness wound (7.5 mm×7.5 mm) was created in the flank skin of each experimental animal. Wounds were then dressed with a 1.5×1.5 cm pad of encapsulated gauze moistened with a fixed volume of sterile saline solution. Wounds were allowed to heal without intervention for a period of 4 days, other than the replacement of saline moistened gauze and film dressings as required.

On day 4 dressings were removed. For the PDT treated group 100 mg of 0.266 mg/mL 3,7-bis(N,N-dibutylamino) phenothiazin-5-ium bromide cream was applied to the wound The wound was then covered and left for 6 minutes and 40 seconds. Following this, the wound was illuminated with 5 688 nm light, at a fluence rate of 125 $mW/cm^2$ to give a light dose of 25 $J/cm^2$. No drug or light was given to the control animals.

Dressings were reapplied immediately after treatment and subsequently on post-wounding days 7 & 10.

Immediately after wounding (day 0) and subsequently on days 4 and 7 all the wounds were digitally photographed together with a calibration/identity plate.

Image Pro image analysis software (version 4.1.0.0, obtained from Media Cybernetics, USA) was used to calculate wound closure from wound images in each of the experimental groups over time. For each wound at each time point—open wound area was measured and expressed in terms of % wound area relative to day 4 (treatment day).

|  | % wound area | |
| --- | --- | --- |
|  | Treatment day | 3 days post treatment |
| Control non diabetic mice | 100 | 48 |
| Control diabetic mice | 100 | 71 |
| PDT treated diabetic mice (500 µM 3,7-bis(N,N-dibutylamino)phenothiazin-5-ium bromide in Unguentum M and 25 J/cm$^2$) | 100 | 46 |
| Vehicle and light treated diabetic mice (Unguentum M and 50 J/cm$^2$) | 100 | 67 |

6 animals were included in each group.

Thus in combination with light 3,7-bis(N,N-dibutylamino)phenothiazin-5-ium bromide provides a substantial increase in the rate of wound healing when the control diabetic mice and treated diabetic mice are compared: 67% wound area remaining vs. 46% remaining respectively. In addition the wound healing in treated diabetic mice was improved and was comparable to the wound healing in the control non diabetic mice: 46% wound area remaining vs. 48% remaining respectively.

Example 2

A Study to Investigate the Effect of 3,7-Bis(N,N-Dibutylamino)Phenothiazin-5-Ium Bromide PDT on Wound Healing in Wistar Rat 3,7-bis(N,N-dibutylamino)phenothiazin-5-ium bromide was solubilised in ethanol to give a concentration of 10 mg/ml. This was diluted in Unguentum M: 80% water, to give creams with final concentrations of 100 µM or 500 µM of 3,7-bis(N,N-dibutylamino)phenothiazin-5-ium bromide.

Treatment Method

The above creams were used on the closure of full thickness excisional wounds in Wistar rats with exposure to light. The effect of topical application of 50 mg of 3,7-bis(N,N-dibutylamino)phenothiazin-5-ium bromide (at concentrations of 100 µM and 500 µM) followed by photo-activation with 688 nm laser light was investigated and compared to that of application of the drug delivery vehicle (Unguentum M) followed by 688 nm photo-activation. The light dose used was 50 J/cm$^2$. Wound repair was measured in terms of the closure of standardised full-thickness excisional wounds created in the flank skin of adult Wistar rats.

At the lower dose (100 µM) wounds in receipt of light treatment closed more rapidly than similar wounds in receipt of the 3,7-bis(N,N-dibutylamino)phenothiazin-5-ium bromide alone.

At the higher dose of 3,7-bis(N,N-dibutylamino)phenothiazin-5-ium bromide (i.e. 500 µM) wounds closed more rapidly than similar wounds in receipt of the lower dose. From gross examination of wound and wound margin tissue—no adverse tissue responses were noted consequent to any treatment regime followed in this study.

Example 3

A Clinical Study to Investigate the Effect of 3,7-Bis(N,N-Dibutylamino)Phenothiazin-5-Ium Bromide PDT on the Wound Healing of Chronic Ulcers Materials and Methods After ethical review board approval and written informed participant consents were obtained, patients were recruited, provided they satisfied the ethically approved inclusion criteria. MHRA approval had been obtained.

Patients were recruited who had chronic non healing leg ulcers or diabetic foot ulcers. These patients had shown little or no wound healing for a number of weeks prior to treatment.

Procedure

For the treatment 3,7-bis(N,N-dibutylamino)phenothiazin-5-ium bromide, formulated in ethanol and Unguentum M as described in Example 2 above at 500 µM, was applied topically to the ulcer surface and surrounding ulcer margin (5 mm) giving a cream depth of up to 5 mm. The ulcer was then left, not occluded, but in minimal lighting, for 15 minutes. After this pre-incubation time, the cream was rubbed into the ulcer so underlying skin/tissue could be seen through the cream. If this was not possible excess cream was removed. The ulcer was then illuminated using a broad band CureLight lamp (obtainable from PhotoCure) at a fluence rate of 20-50 mW/cm$^2$ giving a total light dose of 50 J/cm$^2$.

The ulcer area was measured pre treatment and after 1 week and one month.

Results

There was a reduction in the area of the treated ulcers following the photodynamic treatment. This is shown in Table 1.

TABLE 1

Percentage reduction in ulcer area after 1 week and 1 month compared to pre treatment.

| Patient | Percentage reduction at 1 week | Percentage reduction at 1 month |
| --- | --- | --- |
| 1 | 0 | 10 |
| 2 | Not measured | 50 |
| 3 | 23 | 34 |
| 4 | 8 | 13 |
| 5 | 14 | 8 |

Example 4

A Study to Investigate the Effect of 100 µM and 500 µM 3,7-Bis(N,N-Dibutylamino)Phenothiazin-5-Ium Bromide on Wound Healing in the Wistar Rat Materials and Methods On day 0, animals were anaesthetised and a single standardised full thickness wound (7.5 mm×7.5 mm) was created in the flank skin of each experimental animal. Wounds were dressed with a 1.5×1.5 cm pad of encapsulated gauze moistened with a fixed volume of sterile saline.

Wounds were allowed to heal without intervention for a period of 4 days, other than the replacement of saline moistened gauze and film dressings, as required.

On day 4 standard secondary dressings were removed. 100 mg of 100 µM or 500 µM 3,7-bis(N,N-dibutylamino)phenothiazin-5-ium bromide cream was applied to the wound.

The wounds were not illuminated. The area of the wounds were measured prior to treatment (day 4) and on day 6, 8 and 10.

| | % Wound area remaining, no light | | |
|---|---|---|---|
| | 2 days post treatment | 4 days post treatment | 6 days post treatment |
| 100 μM | 62 | 33 | 25 |
| 500 μM | 62 | 30 | 19 |

In control tests the cream vehicle used alone had no effect on wound healing. In general terms the wounds heal faster at a 500 μM concentration than at 100 μM.

Example 5

Phase IIa Randomised, Placebo Controlled Trial to Investigate Wound Healing Using Photodynamic Therapy in Chronic Leg Ulcers Trial Design 16 patients with chronic leg ulcers were recruited for the study. All patients had ulcers that had been present for at least 3 months prior to treatment. After randomisation, 8 patients were treated with 3,7-bis(N,N-dibutylamino)phenothiazin-5-ium bromide PDT and 8 patients were treated with placebo. Ulcer area was measured before treatment and at 1 week, 1 month, 2 months and 3 months post treatment using a Visitrak system. Photographs were taken of the ulcers before treatment and at 24 h, 1 week, 1, 2 and 3 months post treatment.

Methodology

Placebo cream was Unguentum Merck: water (1:2). 3,7-bis(N,N-dibutylamino)phenothiazin-5-ium bromide cream was 500 μM 3,7-bis(N,N-dibutylamino)phenothiazin-5-ium bromide in Unguentum Merck:water (1:2). For the treatment a 1 mm depth of cream was spread over the surface of the ulcer. The ulcer was then left, occluded under film, shielded from light for 15 minutes. At the end of the 15 minute incubation, excess cream was removed and the ulcer was illuminated using a CureLight 01 (obtainable from Photocure) at a light dose of 50 J/cm$^2$.

Results: Chronic Leg Ulcers

Better healing, as measured by the size of the wound, was found in patients with chronic leg ulcers treated with 3,7-bis(N,N-dibutylamino)phenothiazin-5-ium bromide compared to those treated with placebo. At 2 months, 2 out of 8 (25%) patients who received 3,7-bis(N,N-dibutylamino)phenothiazin-5-ium bromide showed complete wound healing compared to none of those who received placebo. At 3 months, 4 out of 8 (50%) patients who received 3,7-bis(N,N-dibutylamino)phenothiazin-5-ium bromide showed complete wound healing compared to 1 out of 8 (12.5%) patients who received placebo.

Although any methods and materials, similar or equivalent to those described herein, can be used in the practice or testing of the present invention, the preferred methods and materials are described herein. All publications, patents and patent applications cited herein are incorporated herein by reference for the purpose of disclosing and describing specific aspects of the invention for which the publication is cited.

What is claimed is:

1. A phenothiazinium compound of Formula (1)

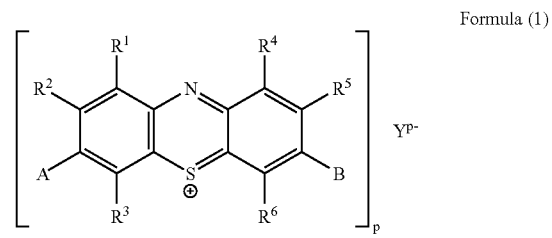

wherein:
each $R^1$-$R^6$ is independently is selected from H, optionally substituted $C_{1-6}$-alkyl, F, Cl, Br and I;
A and B are independently selected from:

Q is selected from optionally substituted $C_{1-4}$-alkyl;
Z is selected from $C(R^a)_2$, O, S, $SO_2$, and $NR^a$ in which $R^a$ is selected from H and optionally substituted $C_{1-4}$-alkyl;
Y is a counteranion selected from F$^-$, Br$^-$, Cl$^-$, I$^-$, $NO_3^-$, SCN$^-$, $ClO_3^-$, $ClO_4^-$, $IO_3^-$, $BF_4^-$, $HSO_4^-$, $H_2PO_4^-$, $CH_3SO_4^-$, $N_3^-$, $SO_4^{2-}$, $HPO_4^{2-}$, $PO_4^{3-}$, acetate, lactate, citrate, tartrate, glycolate, glycerate, glutamate, β-hydroxyglutamate, glucouronate, gluconate, malate and aspartate; and
p is 1, 2 or 3,
in which the optional substituents for any one of $R^1$ to $R^6$, $R^a$ and Q are independently selected from Ph, F, Cl, Br, I, OH, $OC_{1-4}$-alkyl, CN, $OCOC_{1-4}$-alkyl, cyclohexyl, methyl-substituted cyclohexyl, cyclopentyl, methyl-substituted cyclopentyl, COOH, $COOC_{1-4}$-alkyl, and $SO_3H$.

2. A pharmaceutical composition comprising a phenothiazinium compound according to claim 1 and a pharmaceutically acceptable diluent or excipient.

3. A method for promoting wound healing comprising
applying or administering to a wound site to be treated in an animal an effective amount of phenothiazinium compound of Formula (1); and optionally exposing the wound site to light, wherein:
each $R^1$-$R^6$ is independently selected from H, optionally substituted $C_{1-6}$-alkyl, F, Cl, Br and I;
A and B are independently selected from:

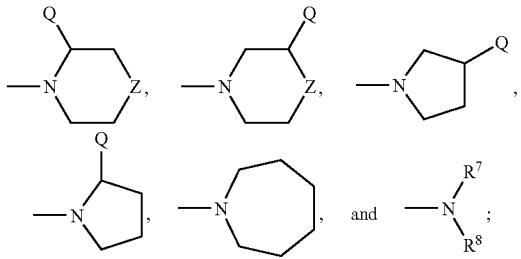

Q is selected from H and optionally substituted $C_{1-4}$-alkyl;

Z is selected from $C(R^a)_2$, O, S, $SO_2$, and $NR^a$ in which $R^a$ is selected from H and optionally substituted $C_{1-4}$-alkyl;
$R^7$ and $R^8$ are independently selected from optionally substituted $C_{3-6}$-alkyl delete the phrase;
Y is a counteranion selected from $R^-$, $Br^-$, $Cl^-$, $I^-$, $NO_3^-$, $SCN^-$, $ClO_3^-$, $ClO_4^-$, $IO_3^-$, $BF_4^-$, $HSO_4^-$, $H_2PO_4^-$, $CH_3SO_4^-$, $N_3^-$, $SO_4^{2-}$, $HPO_4^{2-}$, $PO_4^{3-}$, acetate, lactate, citrate, tartrate, glycolate, glycerate, glutamate, β-hydroxyglutamate, glucouronate, gluconate, malate and aspartate; and
p is 1, 2 or 3,
in which the optional substituents for any one of $R^1$ to $R^8$, $R^a$ and Q are independently selected from Ph, F, Cl, Br, I, OH, $OC_{1-4}$-alkyl, CN, $OCOC_{1-4}$-alkyl, cyclohexyl, methyl-substituted cyclohexyl, cyclopentyl, methyl-substituted cyclopentyl, COOH, $COOC_{1-4}$-alkyl, and $SO_3H$.

* * * * *

UNITED STATES PATENT AND TRADEMARK OFFICE
CERTIFICATE OF CORRECTION

PATENT NO. : 7,407,953 B2
APPLICATION NO. : 11/723523
DATED : August 5, 2008
INVENTOR(S) : Stanley Beames Brown et al.

Page 1 of 1

It is certified that error appears in the above-identified patent and that said Letters Patent is hereby corrected as shown below:

Title Page

Related U.S. Application Data insert

Item (63)   Continuation-in-part of Application No. PCT/GB05/03536, filed on September 14, 2005

Title Page

Foreign Application Priority Data insert

Item (30)   September 20, 2004   (GB) . . . . . . . . . . . . . . . . . 0420888.0

Signed and Sealed this

Twenty-third Day of December, 2008

JON W. DUDAS
*Director of the United States Patent and Trademark Office*